United States Patent [19]

Dell'Acqua et al.

[11] Patent Number: 4,461,768

[45] Date of Patent: Jul. 24, 1984

[54] ANTI-INFLAMMATORY 1,2-BENZOTHIAZINES

[75] Inventors: Ernani Dell'Acqua; Tiberio Bruzzese; Lorenzo Ferrari, all of Milan, Italy

[73] Assignee: SPA Società Prodotti Antibiotici S.p.A., Milan, Italy

[21] Appl. No.: 439,272

[22] Filed: Nov. 4, 1982

[30] Foreign Application Priority Data

Nov. 12, 1981 [IT] Italy ............................... 24993 A/81

[51] Int. Cl.$^3$ .................... C07D 417/12; A61K 31/54
[52] U.S. Cl. ........................................ 424/246; 544/49
[58] Field of Search .......................... 542/427; 544/49; 424/246

[56] References Cited

U.S. PATENT DOCUMENTS 3,900,470 8/1975 Rasmussen ............................. 544/49
3,925,371 12/1975 Rasmussen ............................. 544/49

Primary Examiner—John M. Ford
Attorney, Agent, or Firm—Dennison, Meserole, Pollack & Scheiner

[57] ABSTRACT

A new benzothiazine derivative, that is N-(2-pyridyl)-2-methyl-4-cinnamoyloxy-2H-1,2-benzothiazine-3-carboxamido 1,1-dioxide has been prepared. Owing to its peculiar ester structure, obtained by condensation with cinnamic acid, the new product is endowed with so outstanding pharmacological and toxicological activities, particularly with reference to its tolerableness, to make it a therapeutically valuable anti-inflammatory drug.

2 Claims, No Drawings

ANTI-INFLAMMATORY 1,2-BENZOTHIAZINES

The present invention relates to a new benzothiazine derivative provided with antiphlogistic and analgesic activity.

Compounds having a benzothiazine structure and endowed with analgesic and anti-inflammatory activity have already been described in U.S. Pat. Nos. 3,591,584 and 4,074,048 wherein a series of 3,4-dihydro-4-keto-2H-1,2-benzothiazine-3-carboxamido 1,1-dioxide compounds, structurally related by their tautomeric structure to their corresponding 4-hydroxy derivatives, have been reported. By esterifying the hydroxy group in 4-position to form their acetyl derivatives, it can be noticed however, as published in J. Med. Chem. 16, 44, 1973, a considerable lowering in the anti-inflammatory activity of such compounds (Table I, compounds 2 and 7). Accordingly, the formation of an ester bond, with a consequent stabilization of the tautomeric enolic form, should be considered as having opposite effect on the pharmacological activity of the starting compounds.

Many acylated derivatives we prepared starting from the well known N-(2-pyridyl)-2-methyl-4-hydroxy-2H-1,2-benzothiazine-3-carboxiamido-1,1 dioxide of formula:

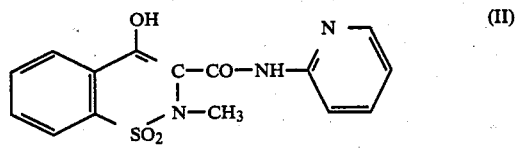

have experimentally confirmed such a conclusion. As a rule all the prepared products showed an irreparable lowering of the therapeutical efficacy unless the ester bond was so weak to make the biological results, as regards the observed activity-toxicity, exactly superimposable to those obtained with the starting material.

Consequently the attempted acylation procedure for obtaining a benzothiazine derivative endowed with lower toxicity and/or gastric damage than the starting material seemed therefore not to be a feasible way.

We have now surprisingly found, and this is an object of the present invention, that our claimed new ester compound, which is N-(2-pyridyl)-2-methyl-4-cinnamoyloxy-2H-1,2-benzothiazine-3-carboxamido 1,1-dioxide, of formula:

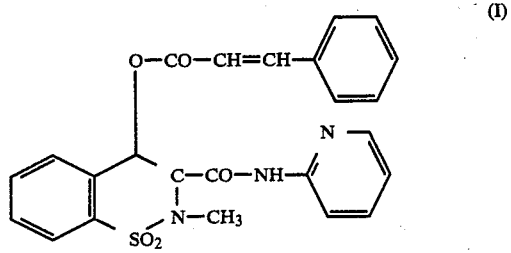

not only is devoid of the above reported ester disadvantages but, being also endowed with higher tolerableness and anti-inflammatory-analgesic activity than the starting material of formula (II), shows a therapeutic index considerably higher than this last one. Compound (I), which is the object of the present invention, is a new compound not previously described in the literature. It appears as a crystalline, colorless solid melting at 157°–158° C., very sparingly soluble in water, sparingly soluble in ethyl acetate, ethanol, diethyl ether, freely soluble in dichloroethane or dimethylformamide.

The synthesis of the claimed product can be performed by different procedures.

The esterification step of the starting N-(2-pyridyl)-B 2-methyl-4-hydroxy-2H-1,2-benzothiazine-3-carboxamido 1,1 dioxide can be carried out, for example, by reaction with cinnamoyl chloride, preferably in the presence of pyridine or triethylamine as acceptors of the hydrogen chloride formed during the esterification process. As reaction solvent an excess of the organic base can be used or, in case, specific solvents such as dimethylformamide. The reaction temperature ranges can vary at from 0° C. to the boiling point of the used solvent, preferably at room temperature of slightly above. The reaction time, according to the other experimental variables, can vary from 15 minutes to 2 hours and only rarely the reaction time has been prolonged to 12 hours. The obtained product is isolated by methods known to those skilled in the art, for example by adding to the reaction mixture an excess of water to precipitate the solid product which is successively recovered by filtration. Independently from the followed eaction process, the product can be obtained with a high standard of purity and, if desired, it can be still purified by crystallization from a suitable solvent such as ethyl acetate.

The biological activities of the new claimed compound of formula (I) have been compared with those of well known antiflogistic and analgesic drugs as well as with those of the starting material (II), which, itself, is used in the clinical practice.

Compound (I) was administered p.o. during 7 days to a group of Swiss mice (18–20 g), while to a control group, under similar experimental conditions, the starting compound (II) was given.

For compound (I) a $LD_{50} > 2000$ mg/kg was found while the starting material (II) shows a $LD_{50} = 250$ mg/kg (192–325).

The analgesic activity of compound (I) has also been checked up on the mice by the phenilquinone "writhing" method according to Hendershot (J. Pharm. Exp. Therap., 125, 237, 1959). After 1 hour from the drug administration (5 mg/kg p.o.), the percent protection for the animals was found to be 50%, said value being exactly superimposable with that obtained using the reference compound II at equivalent dose. When however the analgesic activity was evaluated on the rat, following the classic method of Randall-Selitto (Arch. Int. Pharmac., CXI, 409, 1957), the ester compound (I) showed higher efficacy than compound (II). As a matter of fact the pain threshold (pain tolerance of the inflammed paw) for compound (I) was higher than the reference compound (II) when equal doses of drugs and equal experimentation times were used. (10–40 mg/kg p.o.; 1–5 hours).

The anti-inflammatory activity has also been studied following the method of Winter (Proc. Soc. Exp. Biol. Med., 111, 544, 1962). 0.2 ml of 1% carrageenin was injected into the plantar aponeurosis of a rat paw to cause oedema which was counteracted by a contemporaneous administration of the product at dose of 10–40 mg/kg p.o.

The product's efficacy was verified at fixed times (1–5; 24 hours) by platismography. The obtained results for compound (I) were at least comparable with those obtained for the starting material (II), used as reference compound. Either the above mentioned test results or supplementary activity experimentations on the antipyretic activity and tolerableness (subacute toxicity in the rats) agree on a better pharmacological outline for compound (I) when compared with the starting material (II). What must however suitably be emphasized is the marked lowering of the ulcerogenic effect of the starting material (II) when esterified to give compound (I). As it is well known all anti-inflammatory compounds, comprehensive of corticosteroids, acetylsalicylic acid, indomethacin, phenilbutazone, phenilalkanoic acids and so on, show undesirable secondary but practically constant ulcerogenic side-effects. Also the benzothiazine derivatives, as the related compound (II), show an analogous effect which, beginning with a moderate intolerance to the drug, gastric pyrosis etc., goes on progressively to give deep stomach ulcerations and severe hemorrages in the predisposed patients.

The gastric damaging effect of the new compound (I) has been proved on rats fasting from 24 hours. 5 hours later oral administration of the drug the animals were sacrificed and their gastric mucous was observed to evidence any hemorragic streak, lesion or ulcer. Such test, which was performed also and especially in comparison with the reference compound (II), showed for this last one a clear ulcerogenic effect at 0.5–1 mg/kg, whereas compound (I), at a twofold dose, was perfectly tolerated. From the above reported data the obvious conclusion is that the product of the invention can find a large clinical use for curing a number of patologic syndromes when administered by different pharmaceutical compositions suitable for oral, rectal, topical use or, when suitably solubilized, also by parenteral administration.

The optimal dose which can obviously vary in connection with the administration way, with the seriousness of the illness etc. is anyhow between 1 and 50 mg/person, once or twice a day. The product can be administered associated with other drugs when suitable pharmaceutical compositions were prepared. For oral administration the drug can be formulated as tablets, capsules, granulates, syrups and aqueous suspensions. Suitable carriers for the tablets preparation include besides the usual components also starchs and lubricating agents, particularly magnesium stearate. The capsules can be prepared using hard or soft gelatin and contain the active drug alone or in admixture with various diluents, such as lactose, talc, high molecular weight polyethylene glycols etc. The normal or effervescent granulates can advantageously be divided into single dose containers. In the liquid formulations the product is in form of aqueous solution or suspended particles in admixture with sugars (as for the syrups), suspending agents such as carboxymethyl cellulose, alcohols such as ethanol and glycerol, emulsifying and flavouring agents, etc. For rectal administration, the formulations forecast the use of cocoa-butter, fat acids glycerides in admixture with different excipients as usual for said formulations. The topic formulation includes ointments, creams and lotions, whereas the formulation for parenteral administration involves a solution of the active sterilized ingredient by salt formation or by formation of water soluble complexes with pharmaceutically acceptable substances or by means of suitable solvents. The following examples for the synthesis of the active product are intended to illustrate, but not to limit the invention.

EXAMPLE 1

To 150 ml of anhydrous pyridine, 9.9 g (0.03 mol) of N-(2-pyridyl)-2-methyl-4-idroxy-2H-1,2-benzothiazine-3-carboxiamido 1,1 dioxide are added, at room temperature, under stirring. When a clear solution results, 5 g (0.03 mol) of cinnamoyl chloride are added and the stirring is continued for 2 hours at room temperature.

The reaction mixture is poured into water (900 ml) and the colorless crystalline precipitate (13,4 g) is collected. The Cristallization from ethyl acetate (II vol) gives the substantially pure N-(2-pyridyl)-2-methyl-4-cinnamoyloxy-2H-1,2-benzothiazine-3-carboxamido 1,1 dioxide which may be further purified by crystallization to obtain are analitical sample: m.p. 157°–158° C.; TLC on Silica gel Merck $F_{254}$, eluent: dichloromethane-methanol (98:2), Rf=0.69.

Elemental analysis. Calculated for $C_{24}H_{19}N_3O_5S$, C 62,46%; H 4,15%; N 9,11%; S 6,94%. Found for $C_{24}H_{19}N_3O_5S$, C 62,34%; H 4,36%; N 8,81%; S 6,87%.

EXAMPLE 2

To a solution of 5 g (0.015 mol) of N-(2-pyridyl)-2-methyl-4-hydroxy-2H-1,2-benzothiazine-3-carboxamido-1,1 dioxide in dimethyl formamide (75 ml), 2,51 g (0.015 mol) of cinnamoyl chloride are added. The mixture is stirred for 1 hour at room temperature, added with 1.19 g (0.015 mol) of anhydrous pyridine and subsequently diluted with 500 ml of diethyl ether. The precipitated solid is collected by filtration and washed by trituration with ethyl alcohol.

4.9 g of the dry product (I) are obtained, whose chemicophysical constants are superimposable to those obtained for the product as prepared in Example 1.

EXAMPLE 3

To a solution of 5 g (0.015 mol) of N-(2 pyridyl)-2-methyl-4-hydroxy-2H,-1,2-benzothiazine-3-carboxamido 1,1 dioxide in dimethylformamide (50 ml), 2.51 g (0.015 mol) of cinnamoyl chloride and 1.52 g (0.015 mol) of triethylamine are added. The mixture is stirred at room temperature for 30 minutes. The end product of formula I is precipitated by addition fo iethyl ether (500 ml) recovered by filtration, washed by trituration with ethyl aclohol (twice), filtered and finally dried.

The yield of the colorless cristalline product, m.p. 155°–157° C., is 5.15 g. The melting point of the substance does not show any depression in admixture with on autentic sample of (I).

What we claim is:

1. A product, which is N-(2-pyridyl)-2-methyl-4-cinnamoiloxy-2H-1,2-benzothiazine-3-carboxamido 1,1 dioxide, corresponding to the following formula (I):

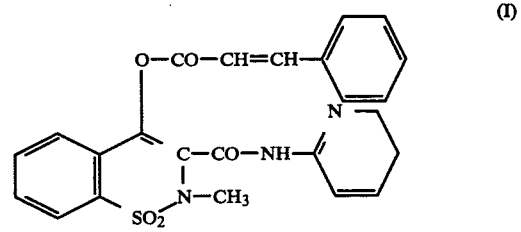

2. Pharmaceutical compositions with anti-inflammatory, analgesic, antipiretic activity which contain a therapeutically effective amount of the product of formula I, according to claim 1, in admixture with a suitable pharmaceutically acceptable carrier thereof.

* * * * *